(12) United States Patent
Petit (10) Patent No.: US 8,876,835 B2
(45) Date of Patent: Nov. 4, 2014

(54) DEVICE FOR POSITIONING AN IMPLANT

(75) Inventor: Dominique Petit, Verton (FR)

(73) Assignee: Safe Orthopaedics, Eragny sur Oise (FR)

( * ) Notice: Subject to any disclaimer, the term of this patent is extended or adjusted under 35 U.S.C. 154(b) by 182 days.

(21) Appl. No.: 13/518,960

(22) PCT Filed: Nov. 17, 2010

(86) PCT No.: PCT/FR2010/000772
§ 371 (c)(1),
(2), (4) Date: Oct. 9, 2012

(87) PCT Pub. No.: WO2011/080404
PCT Pub. Date: Jul. 7, 2011

(65) Prior Publication Data
US 2013/0030541 A1    Jan. 31, 2013

(30) Foreign Application Priority Data

Dec. 28, 2009 (FR) ..................... 09 06369

(51) Int. Cl.
*A61F 2/00* (2006.01)
*A61B 17/58* (2006.01)
*A61B 17/60* (2006.01)
*A61B 19/02* (2006.01)
*A61B 17/70* (2006.01)

(52) U.S. Cl.
CPC ......... *A61B 17/7085* (2013.01); *A61B 19/0271* (2013.01); *A61B 17/7079* (2013.01); *A61B 17/7076* (2013.01); *A61B 19/026* (2013.01); *A61B 2019/0278* (2013.01)

USPC ................ 606/99; 623/16.11; 623/17.11

(58) Field of Classification Search
CPC ................ A61F 2/4611; A61F 2002/4627
USPC ................ 606/99; 623/16.11, 17.11
See application file for complete search history.

(56) References Cited

U.S. PATENT DOCUMENTS

| | | | |
|---|---|---|---|
| 2006/0004376 A1* | 1/2006 | Shipp et al. ............ | 606/99 |
| 2006/0276803 A1 | 12/2006 | Salerni | |
| 2008/0262318 A1 | 10/2008 | Gorek et al. | |
| 2009/0198246 A1* | 8/2009 | Lim et al. ............ | 606/99 |
| 2009/0222045 A1 | 9/2009 | Gorek | |
| 2009/0270874 A1* | 10/2009 | Santarella et al. ............ | 606/99 |
| 2010/0114105 A1* | 5/2010 | Butters et al. ............ | 606/99 |

FOREIGN PATENT DOCUMENTS

| | | |
|---|---|---|
| FR | 2668360 A1 | 4/1992 |
| WO | 9622747 A1 | 8/1996 |
| WO | 2005016183 A1 | 2/2005 |
| WO | 2008097974 A2 | 8/2008 |

* cited by examiner

*Primary Examiner* — Jason-Dennis Stewart
(74) *Attorney, Agent, or Firm* — Bachman & LaPointe, P.C.

(57) ABSTRACT

Equipment for placing an implant comprising an instrument for gripping the implant comprising two portions able to adopt a position of holding the implant and an open position allowing gripping or release of the implant once the latter is implanted, and an element for locking the portions in the holding position, the locking element comprising an attachment device arranged to come into engagement with a complementary attachment device provided in a reception housing formed by the portions in the implant-holding position, the attachment device and the complementary attachment device forming a sliding connection.

23 Claims, 10 Drawing Sheets

DEVICE FOR POSITIONING AN IMPLANT

CROSS REFERENCE TO RELATED APPLICATION

This application claims the priority of the French patent application no 09/06369 filed on Dec. 28, 2009 whose contents are fully incorporated by reference.

BACKGROUND

The invention concerns equipment for placing an implant.

The equipment is intended in particular, but not exclusively, for placing an intersomatic cage, a femoral nail, a rachidian pedicle screw, a disc prosthesis or a rachidian osteosynthesis plate.

In a manner that is conventional per se, the equipments used for placing an implant comprises a threaded part able to cooperate with a tapped part provided in the implant. Patent applications WO 96/22747 and FR 2668360 describe such equipments. Thus mounting the implant on the equipment generally takes place by engaging, by screwing, the threaded part in the tapped bore of the implant. Once the implant is positioned in the planned location, the installation equipment (or placement equipment) is released from the implant by unscrewing the threaded part from the tapped part.

Such equipments do not however allow rapid mounting and demounting of the implant because of the screwing and unscrewing operations.

A second drawback is that locking by means of a threaded part makes it necessary, once the implant is placed, to remove the equipment in order to continue the surgical intervention.

Implant installation equipments are also known, comprising a tubular body provided with two arms having ends for attaching the implant. In this type of equipment, the locking of the implant on the arms is provided by means of an external locking tube, said tube being positioned on the equipment by movement along the external face of the tubular body.

This type of equipment does however has several drawbacks.

A first drawback is that the locking equipment used is not suitable for single-use installation equipment. The arms of the single-use equipment are in fact more fragile through the nature of the material from which the equipment is produced. However, locking the implant by placing a locking piece around the arms accentuates this fragility.

A second drawback is that, apart from the fragility that it confers on the equipment, the presence of a piece external to the tubular body of the equipment leads to relatively bulky equipment.

Another drawback is that locking by means of an external piece is suitable only for an instrument with a straight shape. It cannot be used with equipment of complex shape, which limits the field of application.

SUMMARY OF THE INVENTION

The invention aims to remedy the problems of the prior art by proposing implant installation equipment that is not very invasive, allowing precise implant installation as well as rapid implant engagement and release.

Another aim of the invention is to propose installation equipment make it possible, in addition to the step of installing the implant, to perform supplementary steps occurring during the surgical intervention.

Another aim of the invention is to propose installation equipment that is strong and of optimum size, offering reliable holding of the implant and responding to miniaturisation of the implants and surgical instruments.

To this end, and according to a first aspect, the invention proposes equipment for placing an implant comprising an instrument for gripping the implant comprising two portions able to adopt an implant holding position and an open position enabling the implant to be gripped or released, and an element for locking the portions in the holding position, the locking element comprising attachment means arranged to come into engagement with complementary attachment means provided in a reception housing formed by the portions in the holding position of the implant, said means forming a sliding connection.

Thus the equipment obtained when the gripping instrument and the locking element are assembled offers improved mechanical strength in respect of bending and twisting and ensures good fixing of the implant on the instrument. Moreover, controlling the portions of the instrument providing the gripping of the implant or release thereof by means of an internal element makes it possible to limit the overall size.

Advantageously, the sliding connection is configured to allow a rectilinear translation movement of the locking element with respect to the gripping instrument. According to a variant embodiment, a sliding connection configured to allow a circular translation movement of the locking element with respect to the gripping instrument can be provided.

According to an advantageous configuration, each of the proximal edges is arranged to come into engagement with the implant.

Provision can also be made for the implant to be pre-mounted on the proximal ends of the portions.

According to an advantageous embodiment, the means of attaching the locking element comprise projections in the form of a dovetail able to be inserted in grooves of complementary shape provided in the housing, and vice versa. This makes it possible to offer a bilateral sliding connection. Moreover, the equipment obtained when the gripping instrument and the locking element are assembled offers improved mechanical strength in terms of bending and twisting and ensures holding of the implant.

Advantageously, the portions are formed by two half-shells connected together by a connecting piece.

According to a particular configuration, the locking element and the connecting piece are formed in a single piece.

Provision can also be made for the two half-shells to be joined to each other by a holding ring positioned at the distal end of the said half-shells.

According to a particular embodiment, the equipment comprises an aiming device comprising at least one orifice for aiming and placing a fixing member in association with the implant once the latter is placed. This can be carried either by the locking element or by the gripping instrument.

Advantageously, the equipment comprises at least one second implant pre-mounted on the locking element. According to a particular configuration, the second implant is carried by the aiming device.

Advantageously, the gripping instrument is a mounting tube.

Advantageously, the gripping instrument, when the locking element (4) is positioned in it, forms a guide tube.

Advantageously, the equipment is produced from composite material, polymer, ferrous or non-ferrous alloy or a combination of these different materials. The material used, apart from its biocompatibility, will advantageously be recyclable.

Advantageously, the equipment is for single use.

Advantageously, the equipment can be used with a femoral implant, a rachidian implant of the intersomatic cage type, a rachidian pedicle screw, a disc prosthesis, or a rachidian osteosynthesis plate. It is obvious that the equipment is not limited to such implants.

BRIEF DESCRIPTION OF THE DRAWINGS

Other objects and advantages of the invention will emerge during the following description, given with reference to the accompanying drawings, in which.

For more clarity, identical or similar elements of the various embodiments are marked by identical reference signs in all the figures.

DETAILED DESCRIPTION OF THE PREFERRED EMBODIMENT(S)

In relation to FIGS. 1 to 6, an item of equipment 1 for placing an intersomatic cage 2 between two rachidian vertebrae is described.

The form of the cage used with the equipment according to the invention is not limited to the form illustrated in FIGS. 1 to 6. This is because the form of a cage varies according to the approaches by means of which the surgical intervention takes place (anterior, posterior or lateral approaches) and according to the type of region of the spinal column in which the cage is implanted (cervical, thoracic or lumbar regions). However, and as will be seen below, the cage intended to be associated with the equipment comprises specific means enabling it to be gripped by the equipment in question.

Figure 1:
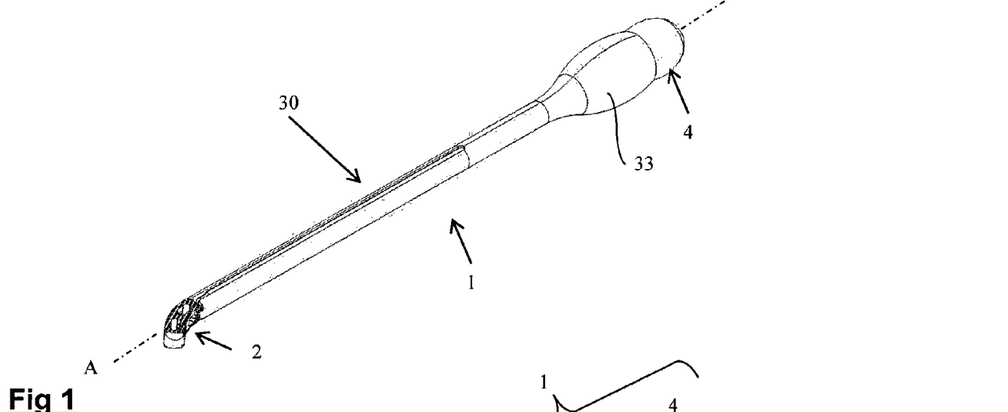
FIG. 1 shows a schematic view of equipment for installing an intersomatic cage according to the invention, the cage being mounted on the equipment.
Figure 2:
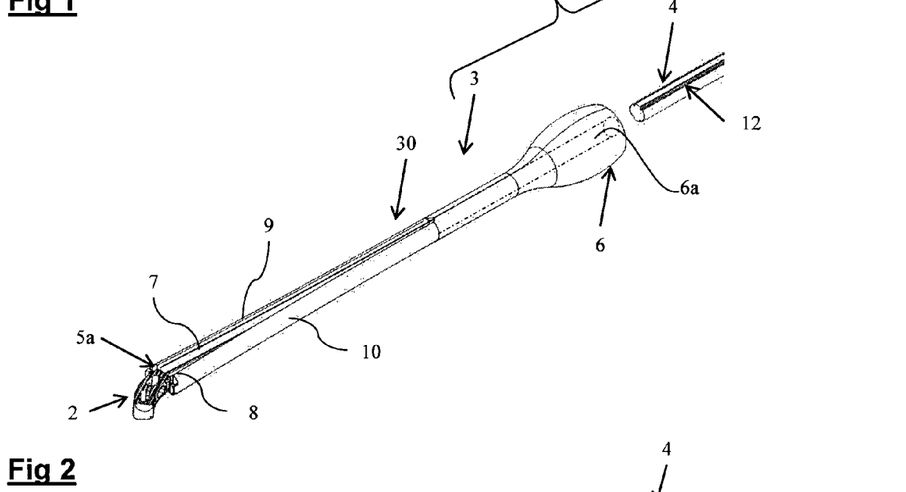
FIG. 2 shows a view of the equipment in FIG. 1 before the insertion of the locking element inside the gripping instrument.

The equipment 1 for placing an intersomatic cage 2 comprises a first element forming an instrument 3 for gripping the cage 2 and a second element forming a locking element 4 enabling the cage 2 to be held by the instrument when it is in engagement with the instrument. The means used for enabling such a holding will be described in detail below.

In the embodiment described, the gripping instrument 3 comprises a mounting tube 30 having a distal end 6 open to enable the locking element 4 to pass and a proximal end 5 arranged to enable the cage 2 to be gripped. "Proximal end" means the end closest to the implant when it is associated with the gripping instrument 3, and "distal end" means the end furthest away from the implant when it is associated with the gripping instrument 3.

As will be seen below, the mounting tube 30 is produced in such a shape and size as to be able to receive the locking element 4 in it.

Advantageously, the mounting tube 30 comprises two longitudinal slots 7, 8 extending from the proximal end 5 in the direction of the distal end 6 so as to delimit two longitudinal portions 9, 10 forming gripping arms. Advantageously, the longitudinal slots 7, 8 are arranged so as to form two gripping arms symmetrical with respect to the axis AA of the mounting tube 30.

In order to facilitate the gripping of the cage 2 but also its release once implanted between the two vertebrae, the slots 7, 8 are sized so that the portions 9, 10 forming arms have a certain flexibility. Flexibility means the ability of the portions 9, 10 forming gripping arms to move away in a direction opposite to the axis AA of the mounting tube 30 and to move closer in the direction of this same axis. It is through this flexibility that the portions 9, 10 are able to adopt a position of holding the implant as illustrated in FIG. 6 and an open position allowing gripping or release of the cage as illustrated in FIG. 4.

Figure 4:
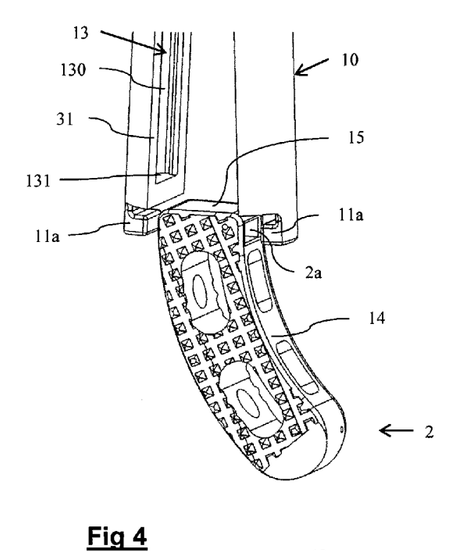
FIGS. 4 to 6 show respectively a detail view of the equipment illustrated respectively in FIGS. 2, 3 and 1.
Figure 5:
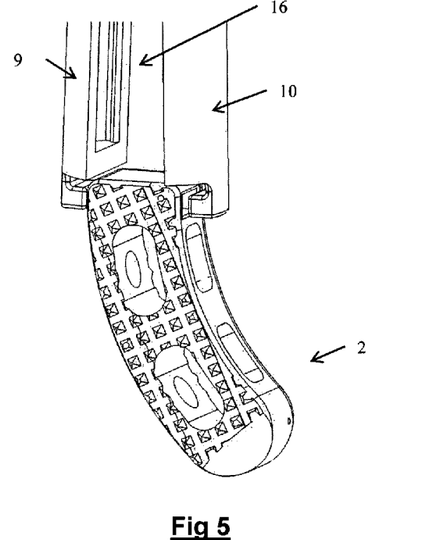
Figure 6:
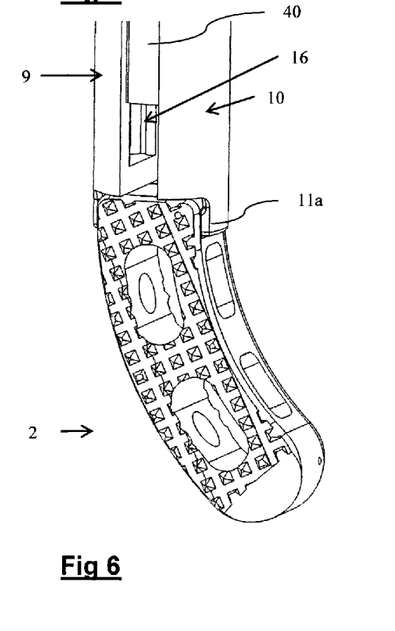
Figure 7:
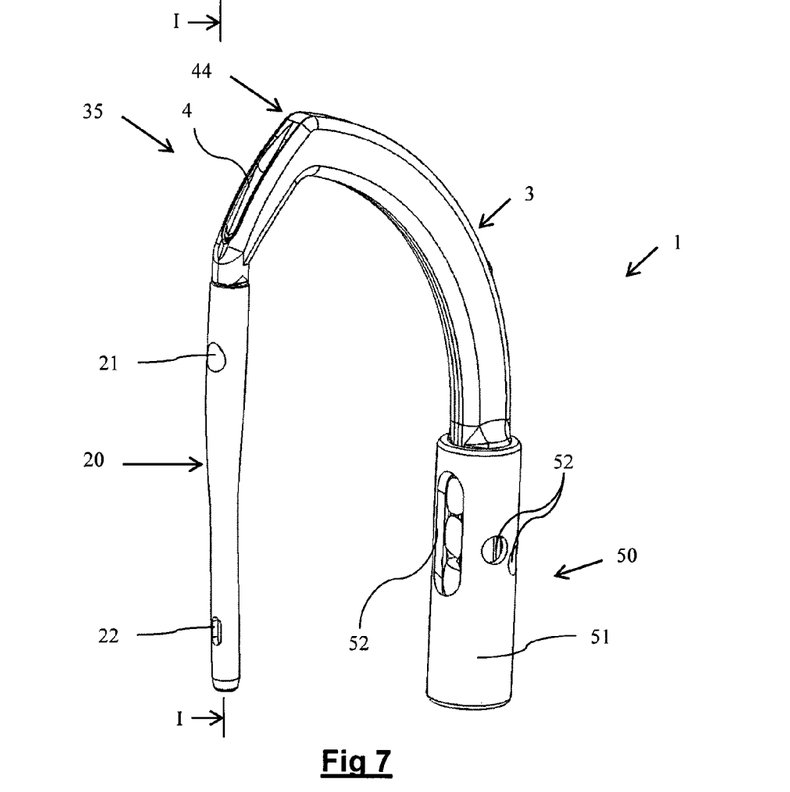
FIG. 7 shows a schematic view of equipment for installing a femoral nail according to the invention.

Advantageously, the proximal end 5 of the mounting tube 30 is arranged to come into engagement with the cage 2 (FIGS. 4 to 6). More particularly, each of the arms 9, 10 comprises, at their end defining the proximal end 5 of the mounting tube, a lug 11a extending towards the inside of the mounting tube 5. The lugs 11a are arranged to come to be housed respectively in a recess 2a of complementary shape provided for this purpose in the cage 2. In the embodiment described, the recesses 2a are provided on the lateral faces 14 of the cage, close to the rear face 15. The term "rear" is defined with respect to the position of the faces of the cage when it is inserted between the vertebrae. Thus the rear face corresponding to the face opposite to the front face by means of which the cage 2 is implanted. It is of course obvious that the invention is not limited, with regard to the means of holding the implant on the mounting tube, to the lugs as illustrated in FIGS. 4 to 6, any other forms of lug or any other implant-holding means being able to be provided without for all that departing from the scope of the invention.

Figure 3:
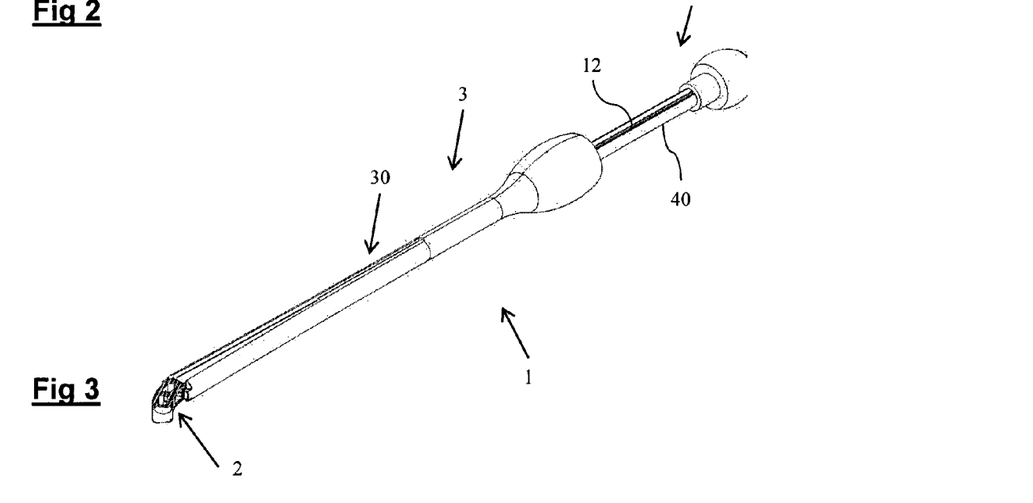
FIG. 3 shows a view of the equipment of FIG. 1, the locking element being partially inserted inside the gripping instrument.

As will be understood from FIGS. 4 to 6, the cage 2 is gripped by the portions 9, 10 moving towards each other. This moving together takes place by insertion of a tubular portion 40 of the locking element 4 inside the mounting tube 30, through the passage opening 6a from distal end 6 to proximal end 5, as illustrated in FIG. 3, until it is in abutment on the face 131 of the mounting tube 3. Once the tubular portion 40 is inserted, the cage 2 is firmly held by the portions 9, 10 of the mounting tube 30. It then does not have any degree of freedom of movement. It should be noted that, between the open position in which the portions 9, 10 are separated from each other (FIG. 4) and the close-together position in which the portions 9, 10 hold the cage firmly (FIG. 6), there exists an intermediate position (FIG. 5), in which the portions 9, 10 are sufficiently close together to prevent disconnection of the cage from the portions 9, 10 but sufficiently separated from each other to allow, where necessary, an adjustment of the position of the cage 2 with respect to the mounting tube 30. This arrangement has a special advantage when the implant holding means are circular in shape, the intermediate position then allowing an adjustment of the angular position.

In order to provide the moving together of the portions 9, 10 of the gripping instrument 3 while providing a rigid connection between the intersomatic cage 2 and the gripping instrument 3, the locking element 4 advantageously comprises attachment means 12 arranged to come into engagement with complementary attachment means 13 provided in a reception housing 16 of the locking element 4 formed by the portions in the implant-holding position, said means forming a sliding connection.

Figure 3A:
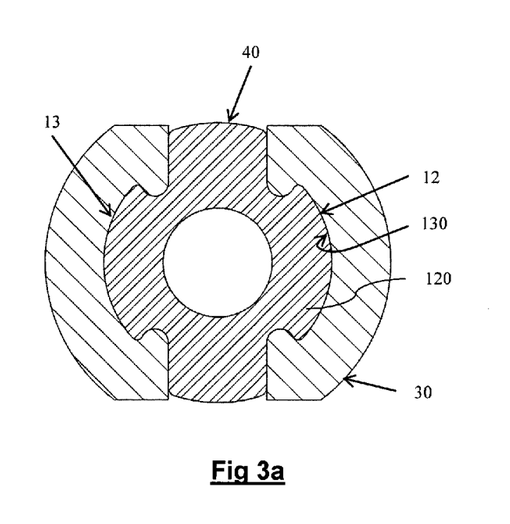
FIG. 3a shows a view in section along the axis III-III of the equipment in FIG. 3.

In a preferred embodiment, the attachment means 12 provided on the tubular portion 40 of the locking element 4 and the attachment means of complementary shape 13 provided inside the mounting tube 30, on the internal face 31 delimiting the reception housing 16, have a profile of the dovetail type, as illustrated in FIG. 3a. The complementarity of the shapes of the tubular portion 40 of the locking element 4 and the portions 9, 10 of the mounting tube 30 has the advantage of stiffening the equipment when the locking element is placed inside the mounting tube and thus improving the strength thereof.

Thus, in the embodiment described, the attachment means 12 carried by the locking element 4 comprise longitudinal projections 120 in the form of a trapezium (contained dovetail), the complementary attachments means 13 carried by the mounting tube 30 being formed by a groove 130 with a shape complementary to that of the projections (containing dovetail). It is of course obvious that equipment can be provided with reversed attachment means (contained dovetail carried by the mounting tube 30 and containing dovetail carried by the locking element 4). Advantageously, the projections are arranged to form a continuous dovetail extending longitudinally between the proximal end 5 and the proximal end 6 of the mounting tube 30.

In the embodiments previously described, the sliding connection is rectilinear (i.e. it is configured so as to allow a rectilinear translation movement of the locking element 4 inside the gripping instrument 3). It is of course obvious that the invention is not limited to the form of the gripping instrument 3 described and therefore to this type of connection. In particular, means of assembling the locking element with the gripping instrument forming a circular sliding connection can be provided.

To facilitate the manipulation of the cage 2 and to provide better gripping of the instrument 3, the mounting tube 30 has, in its distal part, a curved shape 33 configured to provide a handle function.

As will be seen below, it may be advantageous, in anticipation of a conjoint delivery of the cage 2 and installation equipment 1, to provide for the cage 2 to be pre-mounted on the proximal ends 5, 6 of the portions 9, 10.

According to a preferential embodiment, the equipment is for single use.

Advantageously, the installation equipment is produced from composite material, polymer, ferrous or non-ferrous alloy or a combination of these various materials.

In relation to FIGS. 7 to 14, an item of equipment 1 is described for installing a femoral nail 20 and associated fixing screws (not shown) with a view to the consolidation of a femur following a fracture of the associated neck. In this example embodiment, the gripping instrument mainly repeats all the features of the gripping element used with the intersomatic cage 2. The description of these features will therefore not be repeated in its entirety. Only the specific features of the equipment related to its use with a femoral key will therefore be described.

Associated fixing screws means firstly the trochanteric screws used for anchoring the femoral nail 20 at the diaphysis and secondly the cervical screw used for the cephalic anchoring. As for the femoral nail 20, this is a tubular rod, with a slightly curved roughly cylindrical shape.

As in the example previously described, the installation equipment 1 comprises an instrument 3 for gripping the femoral nail 20 and a locking element 4 enabling the femoral nail 20 to be held by the gripping instrument or to be released once the femoral nail is implanted in the planned location.

The gripping instrument 3 is in the form of a tubular body similar to the mounting tube 30 previously described.

The mounting body or tube 30 comprises, at the distal part 32, a handle 33 allowing manual manipulation of the instrument 3. The handle 33, substantially straight, is extended by a curved elongate part 34 the end of which is conformed as a curved head 35. The point of the head 35 defines the proximal end 5 of the mounting tube 30.

In the embodiment described, the mounting tube 30 is formed from two half-shells 30a, 30b with identical shapes and sizes. The two half-shells 30a, 30b are arranged opposite each other and joined to each other at their longitudinal edges. Advantageously, the two half-shells 30a, 30b are arranged so as to allow a reversible connection. In the embodiment described, the connection takes place by clipping the parts 33a, 33b of the two half-shells forming the handle 33. As will be understood later, this assembly at the handle 33 is a primary assembly, the two half-shells 30a, 30b being subsequently connected together by means of a separate connection piece 44. This connecting piece 44 will be described below. It is of course obvious that the two half-shells 30a, 30b can be connected together by any other means, such as by clipping or fitting together or by means of a holding sleeve (not shown). Moreover, the primary assembly may not be provided without for all that departing from the scope of the invention.

Advantageously, the two half-shells 30a, 30b are arranged so that, when they are joined to form the mounting tube 30, a slot 36 emerging inside the mounting tube 30 and extending partly on the head 35 and the elongate curved part 34 is formed. This slot 36 constitutes an opening enabling the connecting piece 44 to pass and to be positioned inside the mounting tube 30, between the two half-shells 30a, 30b.

The connecting piece 44 is formed and sized so as to fit in the reception housing delimited by the internal face of the two half-shells 30a, 30b and the slot 36, thus forming a rigid portion.

Figure 10:
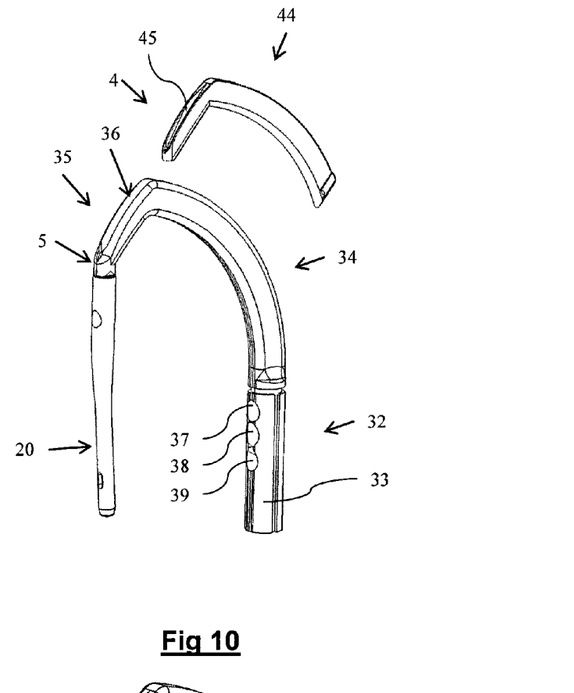
Figure 11:
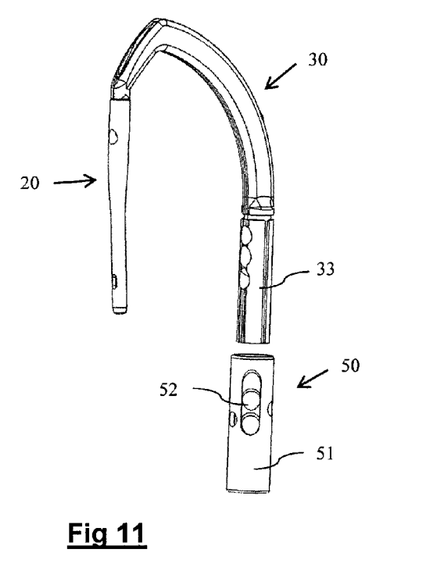
Figure 12:
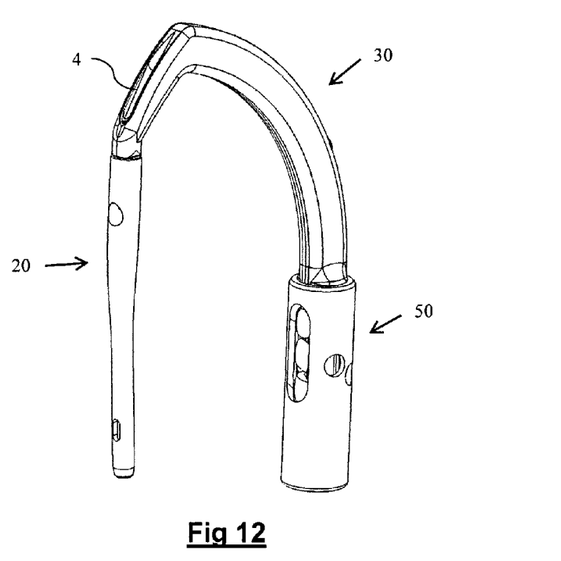

In this embodiment, the locking element 4 preventing any separation of the portions 35a, 35b of the head 35 is formed in a single piece with the connecting piece 44 (FIG. 10). To this end, the connecting piece 44 and the part 35a, 35b forming a head 35 comprises locking means of the dovetail type similar to those described previously.

Figure 9:
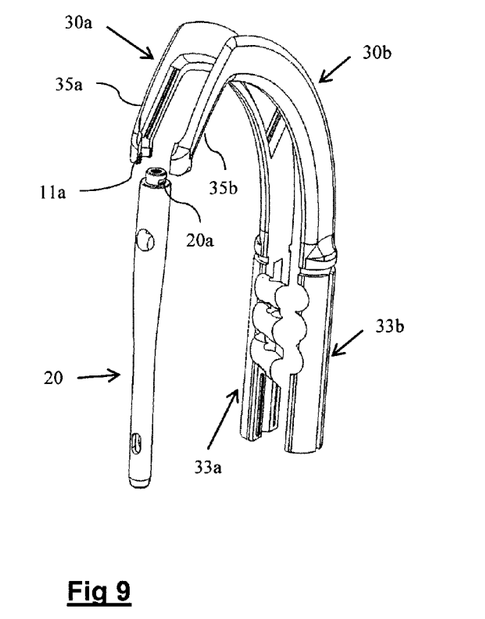
FIGS. 9 to 12 show views showing the steps of mounting the equipment in FIG. 7, the femoral key being fixed to the equipment.

As will be understood from FIGS. 9 and 10, the gripping of the femoral nail 20 is achieved by presenting the two half-shells 30a, 30b disconnected from each other. The gripping of the femoral nail 20 is achieved by bringing the two half-shells 30a, 30b towards each other until they come to be positioned against each other. At that moment, the proximal end of each of the two half-shells defining the proximal end 5 of the mounting tube 30 grips the top end of the nail. The term "top" is defined with respect to the position of the femoral nail 20 when it is implanted in the femur. In other words, the top end corresponds to the end closest to the neck of the femur.

The two half-shells 30a, 30b then form the mounting tube 30. Once the femoral nail 20 is held between the proximal ends of the two half-shells 30a, 30b, the connecting piece 44 is placed in the reception housing 16 by putting in contact and sliding the contained (or containing) dovetails formed on the head portion 45 of the connecting piece 44 in the complementary dovetails formed on the internal face of each of the two half-shells 30a, 30b, at the parts 35a, 35b forming a head 35, in the direction of the proximal end opening 5. Once the connecting piece 44 is fully inserted between the two half-shells 30a, 30b, the separation of the parts 35a, 35b of the two half-shells forming the head is prevented and the fixing of the femoral nail 20 on the gripping instrument 3 ensured.

As in the example previously described, the proximal end 5 of the head 35 is arranged so as to come into engagement with the femoral nail 20. Thus the parts 35a, 35b forming a head, similar to the portions 9, 10 of the equipment previously described, comprise respectively a lug 11a extending towards the inside of the mounting tube 30 and arranged to come to be housed respectively in a recess 20a of complementary shape provided for this purpose in the femoral nail 20. In the embodiment described, the recesses 20a are provided at the top end 25 of the femoral nail 20.

Figure 8:
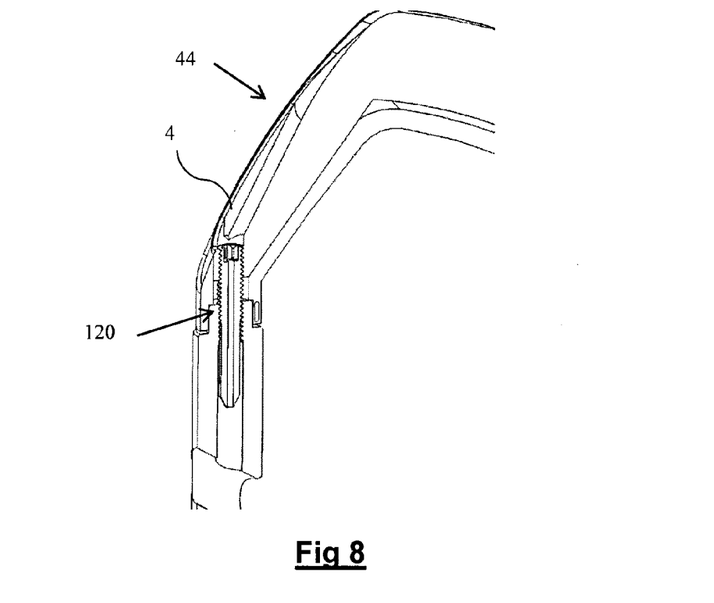
FIG. 8 shows a detail view in section along the axis I-I of the equipment in FIG. 7.

According to a particularly advantageous configuration embodiment, the gripping instrument 3 is provided so as to be able to carry at least a second implant. FIG. 8 illustrates for this purpose the connecting piece 44 provided, at the end of the head portion 45, with a pressure screw 120 intended to lock the trochanteric screw by friction. The pressure screw 120 is fixed by screwing in a threaded-end opening in the head portion 45 of the connecting piece 44. The pressure screw 120 thus previously loaded onto the connecting piece 44, and more precisely onto the locking element 4, thus prevents any disconnection and strengthens the connection. This also prevents any prior demounting at the end of the placing of the locking element. Such an implant preloading also reduces the surgical intervention time.

Advantageously, such an implant preloading allows precise surgical action. It is not always easy during surgery to connect two implants together. The device 1 overall responds to this problem. In this very precise example of an application to a femoral nail 20, the gripping instrument 3 and the connecting piece 44 form a guide for placing the pressure screw 120.

Advantageously, the handle 33 is hollow (FIG. 9). To allow the passage of guides for placing the trochanteric and/or cervical screws, transverse passage holes 37, 38, 39, parallel to each other, are provided on the handle 33. Each hole, in association with one of the bores 21, 22 formed in the femoral nail 20, defines a given angular position for the trochanteric or cervical screws. In the embodiment described, the handle 33 is shown with three transverse passage holes 37, 38, 39 corresponding to three favoured angular positions. It is of course obvious that the handle 33 may be provided with a different number of passage holes.

Figure 13:
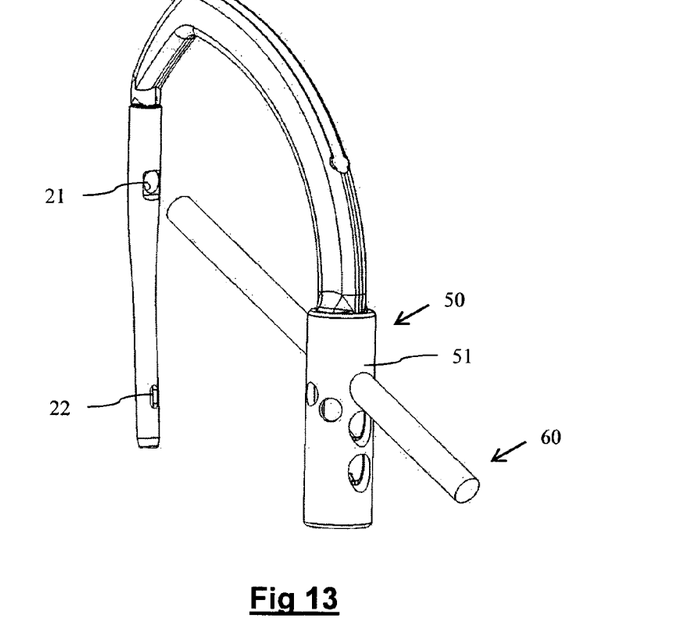
FIG. 13 shows the equipment of FIG. 7 equipped with an aiming device and a guide for positioning a trochanteric screw.
Figure 14:
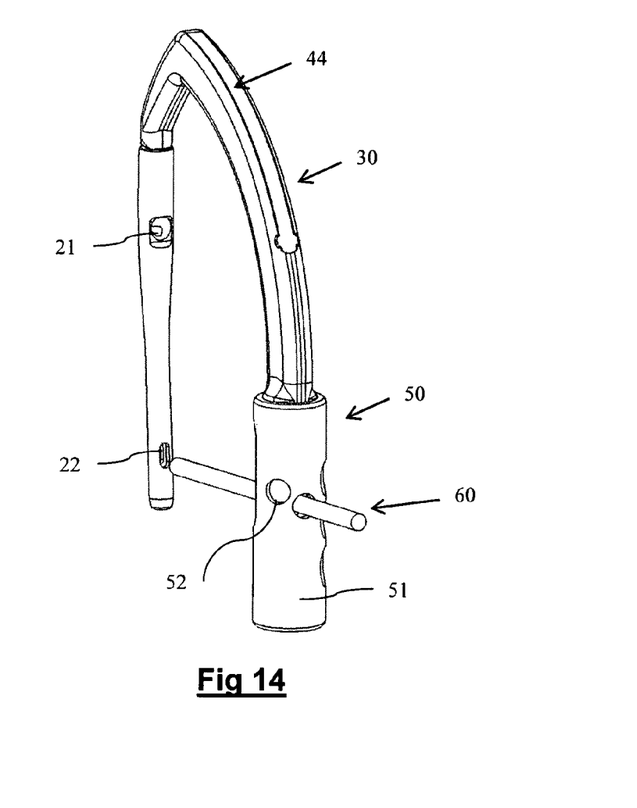
FIG. 14 shows the equipment of FIG. 7 equipped with an aiming device and a guide for positioning a cervical screw.
Figure 15:
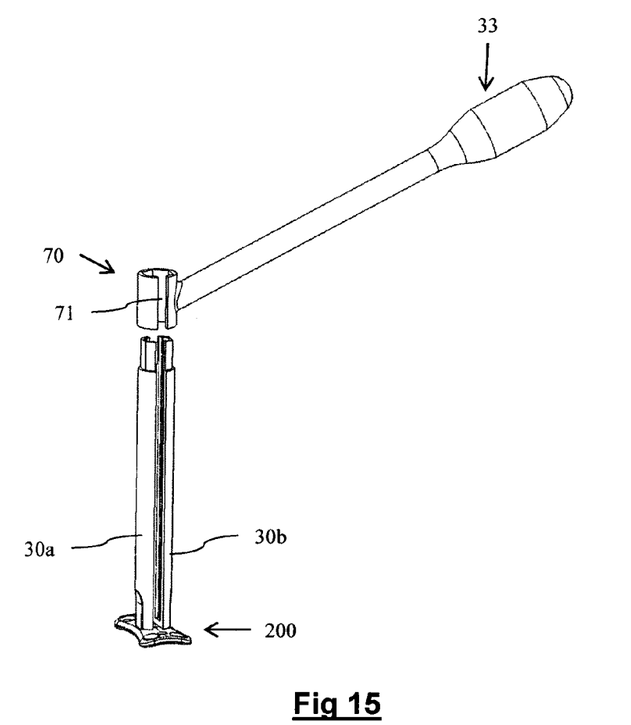
FIG. 15 shows an exploded partial view of equipment for installing an osteosynthesis plate according to the invention, the plate being mounted on the equipment.
Figure 16:
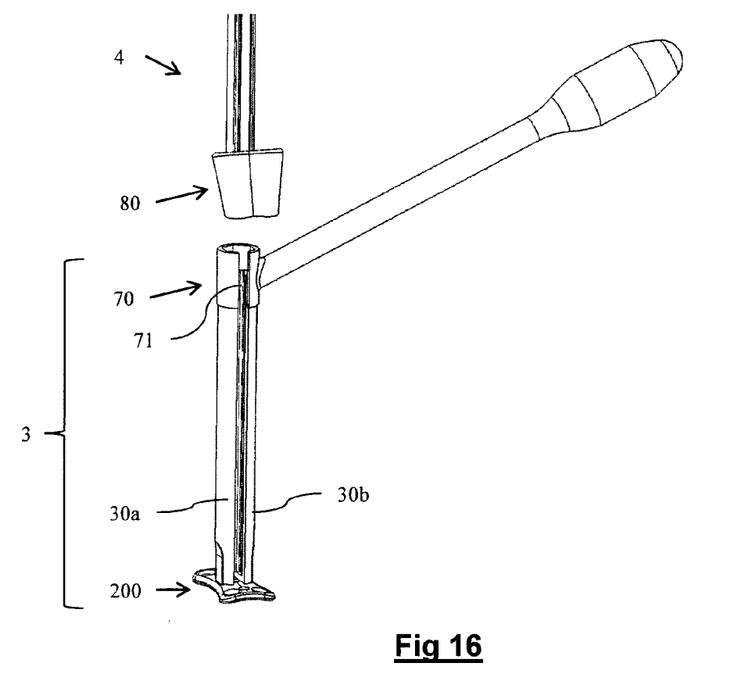
FIG. 16 shows a view of the equipment in FIG. 15, before the insertion of the locking element inside the gripping equipment.

According to a variant embodiment, the gripping instrument 3 comprises an aiming device 50 for aiming the trochanteric and cervical screws. In the embodiment described, the aiming device 50 comprises an aiming ring 51 able to fit on the handle 33. The aiming ring 51 is sized so as to ensure holding thereof on the handle 33 while allowing a rotation movement thereon. Advantageously, the aiming ring 51 comprises several apertures 52 arranged so as to allow, according to the position given to the aiming ring 51 with respect to the handle 33, specific angular positionings of the trochanteric and cervical screws. Thus FIGS. 13 and 14 illustrate the aiming ring 38 with a guide 60 passing through it for passage of the fixing screws, the aiming ring 51 being in the aiming position for the trochanteric screw in FIG. 13 and in the aiming position for the cervical screw (FIG. 14). The presence of an aiming ring 51 thus makes it possible to offer a number of angular positions greater than the three angular positions conventionally provided at the handles.

FIGS. 15 to 23 illustrate equipment 1 used for placing a rachidian osteosynthesis plate 200. As before, the equipment 1 comprises an instrument 3 for gripping the plate 200 and a locking element 4 for providing the holding of the plate 200 by the gripping instrument 3 when it is engaged by the instrument. In the example embodiment described below, the gripping instrument 3 is a combination of the features of the gripping instrument used with the intersomatic cage 2 and the gripping instrument used with the femoral nail. A description of these features will therefore not be repeated in its entirety. Only the specific features of the equipment relating to its use with the osteosynthesis plate will be described.

The form of the plate used with the equipment is not limited to the form illustrated in FIGS. 15 to 23, and this may vary according to the approaches by which the surgical interventions take place (anterior, posterior or lateral approaches) and according to the type of region of the spinal column for which the plate is intended (cervical, thoracic or lumber regions) as well as for any other traumatological general orthopaedic surgery.

In this example embodiment, as for the femoral nail, the gripping instrument 3 is a mounting tube 30 formed by two half-shells 30a, 30b. However, in the present case, the two half-shells are held at a distance from and opposite each other and are connected to each other by means of a holding ring 70 positioned at the distal end of the two half-shells 30a, 30b. Thus formed, the gripping instrument 3 is similar to the mounting tube 30 used with the intersomatic cage 2. Thus the two half-shells correspond respectively to one of the two portions 9, 10 forming a gripping arm and the spacing present between the two half-shells corresponds to the reception housing 16 and to the slots 7, 8. As will be seen below the spacing present between the two half-shells will allow the passage of a locking element provided with an aiming device.

Advantageously, the holding ring 70 comprises a slot extending over the entire length thereof. When the holding ring 70 is placed at the ends of the two half-shells, care will be taken to position the slot 71 in line with the spacing present between the two half-shells to enable a locking element provided with an aiming device to pass.

According to a variant embodiment, the gripping instrument could be formed from a straight tubular body in which a slot has been formed, extending from the proximal opening end as far as the distal opening end.

The holding ring 70 makes it possible to hold the two half-shells 30a, 30b temporarily in the assembled position until the locking element 4 is placed, which will then take over once inserted inside the two half-shells 30a, 30b. The holding ring 70 thus forms a primary holding means.

The gripping instrument 3 comprises a handle 33 arranged to facilitate the manipulation of the mounting tube 30. In an advantageous embodiment, the handle 33 and the holding ring 70 will be secured to each other.

As described previously, the prime function of the locking element 4 is the connection of the half-shells 30a, 30b by means of the sliding connection of the dovetail type.

In the embodiment described, the locking element 4 comprises, at one of the ends thereof, an aiming device 80 for guiding the placing of a bone anchoring element, such as a fixing screw 90, for fixing the osteosynthesis plate 200. Advantageously, the locking element 4 and the aiming device 80 form one and the same piece.

The aiming device 80 comprises aiming orifices 81, each orifice being formed so as to have an aiming axis colinear with one of the apertures 201 formed in the plate 200 and intended to receive a fixing screw 90. In the embodiment illustrated, the aiming device 80 comprises two aiming orifices 81 with colinear aiming axes.

Advantageously, the aiming device is secured to the locking element by a junction portion 82 configured to slide along the slot 71 in the holding ring 70 and between the two half-shells 30a, 30b.

Figure 27:
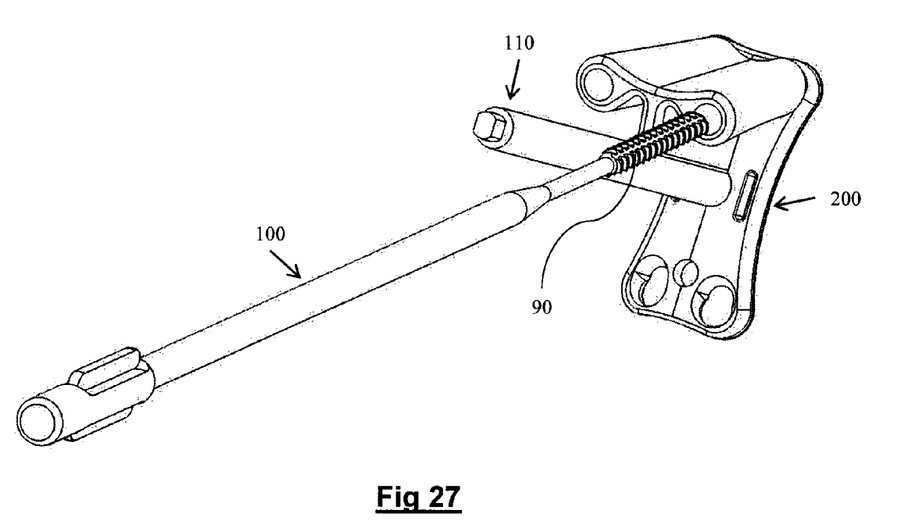
FIG. 27 shows a perspective plan view of the gripping instrument of FIG. 26, the aiming device being shown during use thereof in association with a tap.
Figure 28:
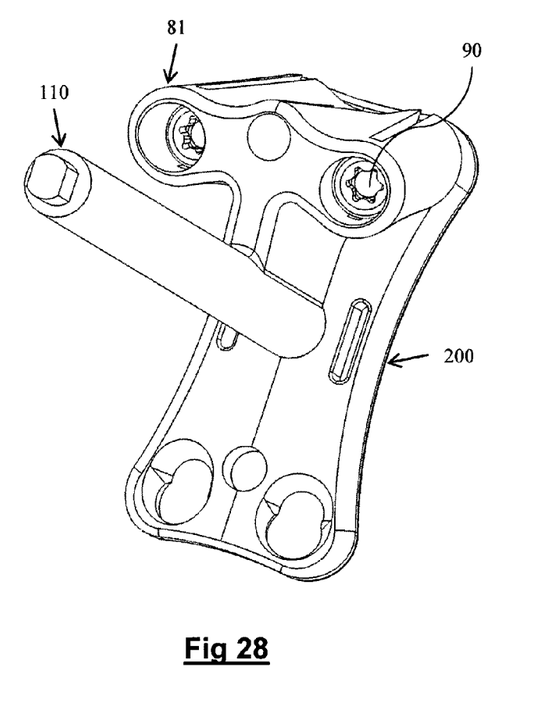
FIG. 28 shows a perspective view of the gripping instrument of FIG. 27, the aiming device being shown equipped with pre-mounted screws.

Advantageously, the aiming orifices 81 are arranged to receive a fixing screw 90 but also so as to allow the passage of taps 100 or any other type of instrument such as bits, probes, screwdrivers, etc. (FIG. 27).

Figure 22:
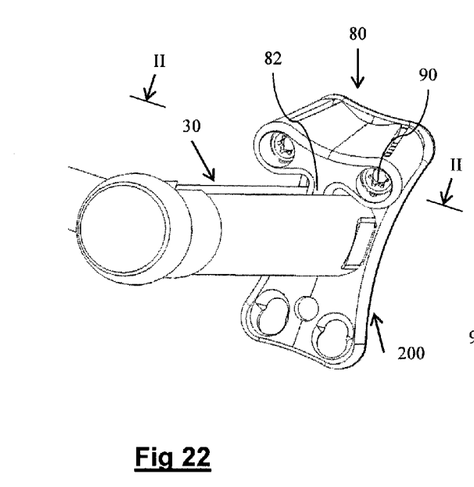
FIG. 22 shows a perspective plan view of the equipment in FIG. 15, the aiming device being shown provided with pre-mounted screws.
Figure 23:
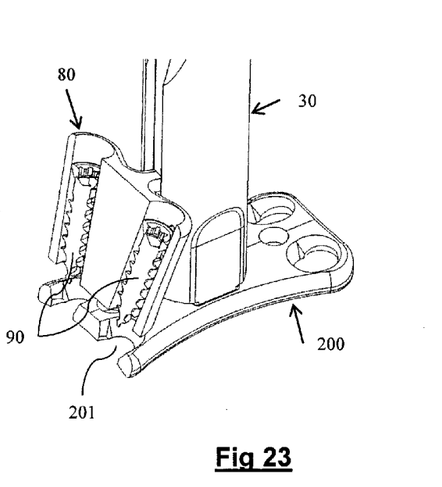
FIG. 23 shows a view in section of the aiming device along the axis II-II in FIG. 22.
Figure 24:
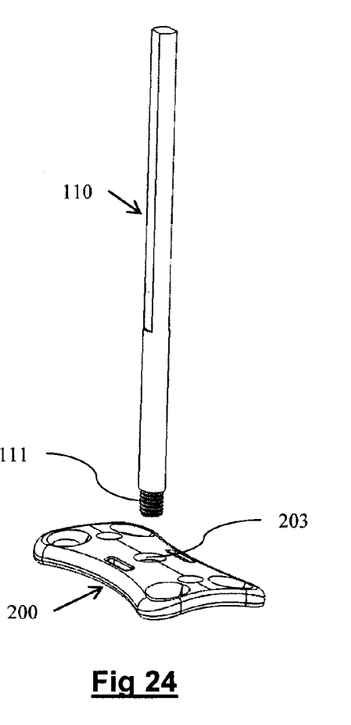
FIGS. 24 and 25 show a perspective view respectively from the side and above of an instrument for gripping an osteosynthesis plate according to one embodiment.
Figure 25:
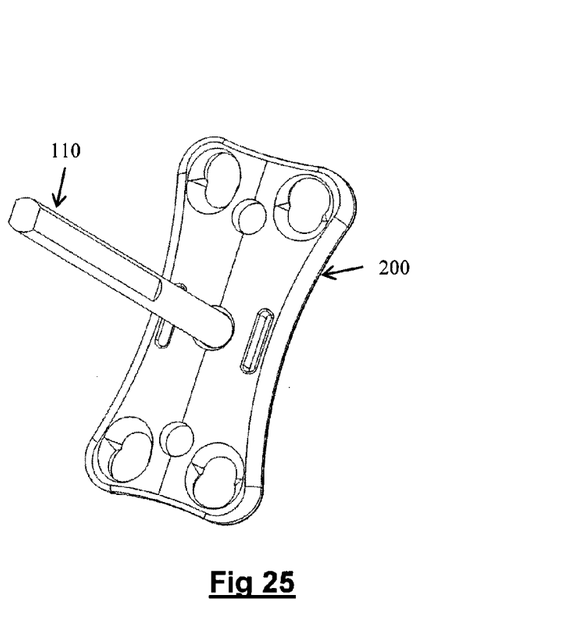
Figure 26:
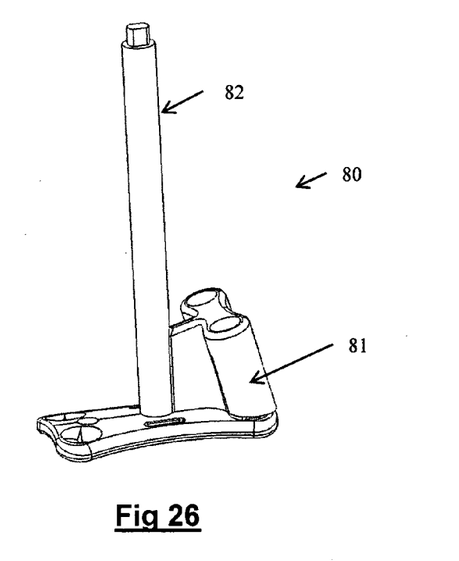
FIG. 26 shows the gripping instrument of FIGS. 24 and 25 provided with an aiming device.

In a particularly advantageous embodiment illustrated by FIGS. 22 and 23, a locking element 4 is provided, comprising an aiming device in which the fixing screws 90 are pre-mounted in the aiming orifices 81. The aiming device then forms a "screw dispenser".

The conjoint presence of an aiming device and pre-mounted fixing screws enables a surgeon to have precise, rapid and simplified action.

Figure 17:
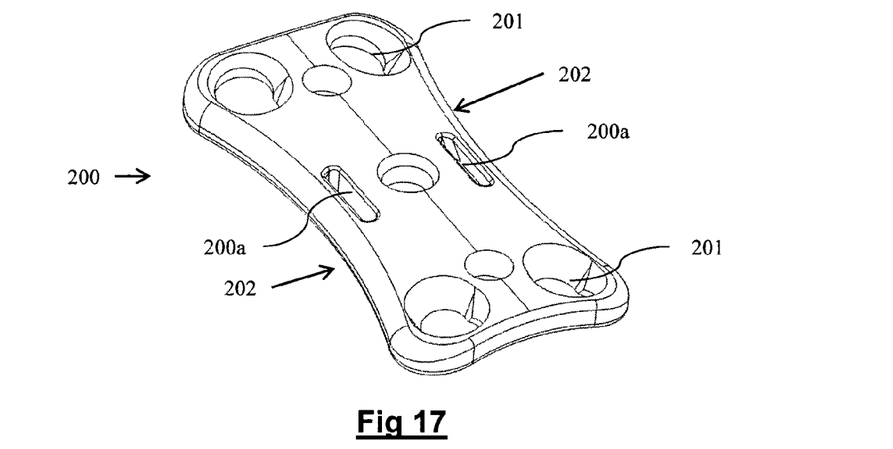
FIG. 17 shows an osteosynthesis plate intended to be associated with the installation equipment in FIG. 15.
Figure 19:
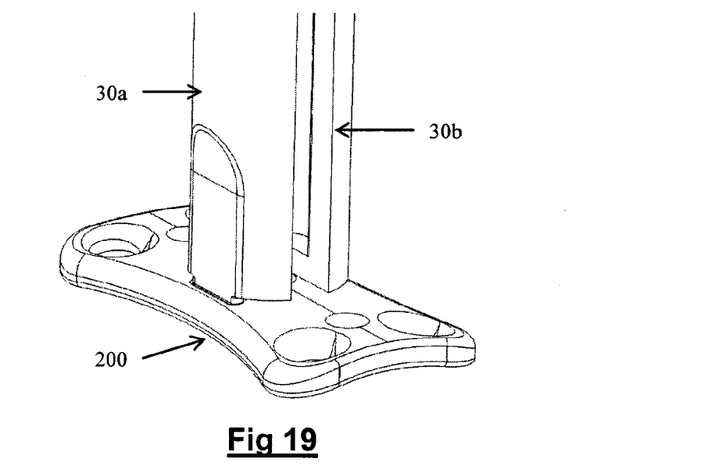
Figure 20:
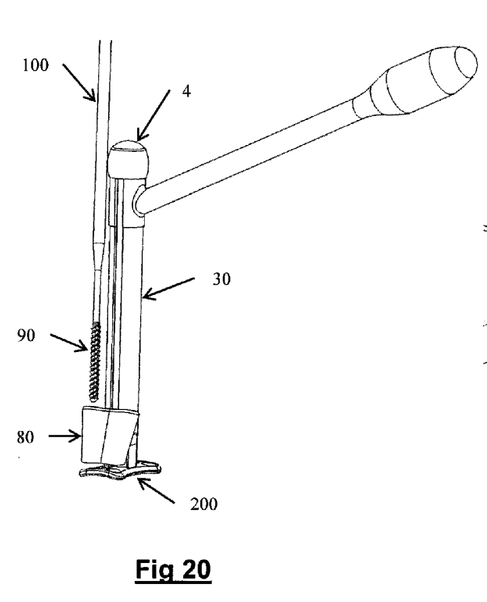
FIGS. 20 and 21 show a perspective view respectively from the side and above of the equipment in FIG. 15, the aiming device of the locking element being shown during use thereof in association with a tap.
Figure 21:
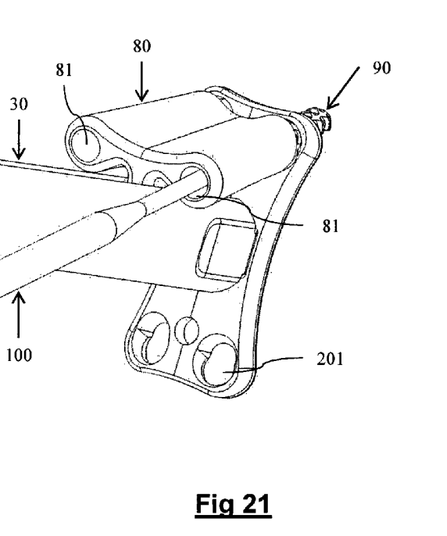

In the example previously described, the proximal element 5 of the mounting tube 30 formed by the proximal ends of the two half-shells are arranged so as to come into engagement with the plate 200. Thus the proximal ends of each of the two half-shells 30a, 30b comprise respectively a lug extending towards the inside of the mounting tube and arranged to come to be housed respectively in a recess with a complementary shape provided for this purpose in the plate 200. In the embodiment described, the recesses are provided at the lateral edges 202 of the plate 200 (FIGS. 17 and 19). "Lateral edges" means the edges extending substantially in the same direction as the longitudinal direction of the plate.

Figure 18:
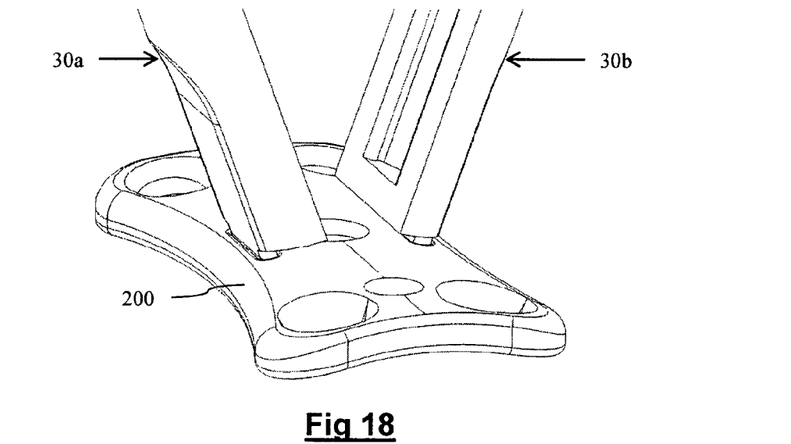
FIGS. 18 and 19 show respectively the osteosynthesis plate in the course of mounting on the gripping instrument and the plate once mounted.

FIGS. 18 and 19 illustrate the mounting of the plate on the gripping instrument. It should be noted, and it will be understood more easily with the example of the plate, that the production of a gripping instrument by means of two separate half-shells has the advantage of facilitating and improving the gripping of the implant.

FIGS. 24 to 28 illustrate a simplified version of the equipment 1 for placing an osteosynthesis plate, the equipment being provided with an aiming device 80 as described previously. The gripping instrument 3 therefore repeats all the features of the gripping instrument for placing a plate previously described. Only the specific features of this equipment are therefore described below.

In this embodiment, the placing equipment 1 comprises a shouldered rod 110 having a threaded end 111 intended to cooperate with a tapped orifice 203 provided for this purpose in the plate 200. In the embodiment described, the tapped orifice 203 is positioned at the centre of the plate 200.

Advantageously, the aiming device 80 comprises a tubular body 82 configured so as to fit on the shouldered rod 110.

For the purpose of current ready to use orientations, the placing equipment according to the invention and the associated implant, once assembled, are advantageously placed in a sterile package in order then to be delivered to hospitals. It will also be advantageous to provide single-use placing equipment. The preparation of such packaging has the advantage of reducing the overall cost of surgery and to guarantee non-contamination from one patient to another. This also has the advantage of reducing the surgical intervention time and consequently proceeding with shorter anesthesia of the patient.

Moreover, it is of course obvious that the application to implants described previously is not limited to the implants previously described. In particular, it may be advantageous to provide equipment according to the invention for placing, for example, bone anchoring means for fixing rachidian osteosynthesis systems and traumatological plates.

The invention is described above by way of example. Obviously a person skilled in the art is in a position to implement different variant embodiments of the invention without for all that departing from the scope of the invention.

The invention claimed is:

1. Equipment for placing an implant comprising:
an instrument for gripping the implant comprising two portions able to adopt a position of holding the implant and an open position enabling the implant to be gripped or released once the implant is implanted, said portions being arranged relative to each other for delimiting a reception housing of a locking element when said portions are in the position of holding the implant, and
the locking element configured to lock the portions in the position of holding the implant, the locking element comprising attachment means arranged to come into engagement with complementary attachment means provided on the portions, said attachment means and said complementary attachment means forming a sliding connection.

2. Equipment according to claim 1, wherein the portions are arranged so as to form, in the implant holding position, a mounting tube, said mounting tube being arranged so as to receive the locking element.

3. Equipment according to claim 2, wherein the mounting tube has an internal face delimiting the reception housing receiving the locking element.

4. Equipment according to claim 1, wherein the portions are able to adopt an intermediate position of adjusting the position of the implant with respect to said portions.

5. Equipment according to claim 1, wherein the sliding connection is configured so as to allow a rectilinear translation movement of the locking element with respect to the gripping instrument.

6. Equipment according to claim 1, wherein the sliding connection is configured so as to allow a circular translation movement of the locking element with respect to the gripping instrument.

7. Equipment according to claim 1, wherein the portions each have a proximal end arranged so as to come into engagement with the implant.

8. Equipment according to claim 7, wherein the implant is pre-mounted on the proximal ends of the portions.

9. Equipment according to claim 1, wherein said attachment means for attaching the locking element comprise projections in the form of a dovetail able to be inserted in grooves with a complementary shape formed in the reception housing, and vice versa.

10. Equipment according to claim 1, wherein the portions are formed by two half-shells connected to each other by a connection piece.

11. Equipment according to claim 10, wherein the locking element and the connecting piece are formed in a single piece.

12. Equipment according to claim 10, wherein the two half-shells are joined to each other by a holding ring positioned at a distal end of said half-shells, said distal end being away from the implant.

13. Equipment according to claim 1, further comprising an aiming device comprising at least one orifice for aiming and placing a fixing member in association with the implant once the implant is placed.

14. Equipment according to claim 13, wherein the aiming device is carried by the locking element.

15. Equipment according to claim 14, wherein the aiming device is carried by the gripping instrument.

16. Equipment according to claim 13, further comprising at least one second implant pre-mounted on the locking element.

17. Equipment according claim 16, wherein the at least one second implant is carried by the aiming device.

18. Equipment according to claim 1, wherein the gripping instrument is a mounting tube.

19. Equipment according to claim 1, wherein the gripping instrument, when the locking element is positioned in the gripping instrument, forms a guide tube.

20. Equipment according to claim 1, wherein the equipment is produced from a composite material, a polymer, a ferrous or non-ferrous alloy or a combination of mixtures thereof.

21. Equipment according to claim 1, wherein the equipment is for single use.

22. Equipment according to claim 1, wherein the implant is a femoral implant.

23. Equipment according to claim 1, wherein the implant is a rachidian implant of an intersomatic cage or a rachidian osteosynthesis plate type.

* * * * *